United States Patent [19]

Lee et al.

[11] Patent Number: 5,032,617

[45] Date of Patent: Jul. 16, 1991

[54] SUBSTITUTED BENZAMIDE RADIOSENSITIZERS

[75] Inventors: William W. Lee; Edward W. Grange, both of Palo Alto; J. Martin Brown, Stanford, all of Calif.

[73] Assignee: SRI International, Menlo Park, Calif.

[21] Appl. No.: 356,673

[22] Filed: May 18, 1989

Related U.S. Application Data

[63] Continuation of Ser. No. 730,761, May 3, 1985, abandoned.

[51] Int. Cl.$^5$ .................. A01N 41/02; A61K 31/255; A61K 31/275
[52] U.S. Cl. ................................ 514/617; 514/619; 514/620; 514/621; 514/622
[58] Field of Search ............... 514/617, 619, 620, 621, 514/622

[56] References Cited

U.S. PATENT DOCUMENTS 3,983,164 9/1976 Thorne et al. .................. 260/473 R
4,371,540 11/1982 Lee et al. ......................... 424/273 R

FOREIGN PATENT DOCUMENTS 0009608 4/1980 European Pat. Off. .
0076463 4/1983 European Pat. Off. .
1230018 4/1971 United Kingdom .

OTHER PUBLICATIONS

Push, "Scientists Eye Draize Test Alternatives" The John Hopkins Center for Alternatives to Animal Testing Newsletter, vol. 3, No. 1, pp. 1–8 (1984).
Dagani, "In-Vitro Methods May Offer Alternatives to Animal Testing" C & EN (Nov. 12, 1984) pp. 25–28.
Jumblatt et al, "A Tissue Culture Model of Ocular Irritancy" ARVO Abstract (1984).
Ubels et al, "Healing of Experimental Corneal Wounds Treated With Topically Applied Retinoids", Am. J. Opthalmol 95:353–358 (1983).
Dagani, "Alternative Methods Could Cut Animal Use in Toxicity Tests" C & EN Oct. 31, 1983, pp. 7–13.
Jumblatt & Neufeld "B-Adrenergic and Serotenergic Responsiveness of Rabbit Corneal Epithelial Cells in Culture", Invest. Opthalmol. Vis. Sci 24:1139–1143 (1983).
Falahee et al "Eye Irritation Testing: An Assessment of Methods and Guidelines for Testing Materials for Eye Irritancy" EPA-560/11-82-001 Oct. (1981).
Gipson et al "Effects of Cytochalasins B & D and Colchicine on Migration of the Corneal Epithelium" Invest. Opthalmol. Vis. Sci. 22:633–642 (1982).
Gipson and Anderson "Effect of Lectins on Migration of the Corneal Epithelium" Invest. Opthalmol. Vis. Sci. 19:341–349 (1980).
Thompson et al "The Effect of An Eye Derived Growth Factor (EDGF) on Corneal Epithelial Regeneration", Exp. Eye Res. 34:191–199 (1982).
Jumblatt et al "Cholera Toxin Stimulates Adenosine 3'5' Monophosphate Synthesis and Epithelial Wound Closure in the Rabbit Cornea" Invest. Opthalmol. Vis. Sci. 19:1321–1327 (1980).
Jumblatt and Neufeld "Characterization of Cyclic AMP-mediated Wound Closure of the Rabbit Corneal Epithelium" current Eye Res. 1:189–195 (1981).
Cintron et al "A Simple Method for the Removal of Rabbit Corneal Epithelium Utilizing n-Heptanol" Opthalmic Res. 11:90–96 (1979).
Jumblatt and Neufeld "A Tissue Culture Model of the Human Corneal Epithelium" (Opthalmic Pharmacology Unit Eye Research Institute & Dept. of Opthalmology Harvard Medical School, Boston, Mass.
Chemical Abstracts, Tenth Collective Index Chemical Substances Azawowaboraw–Benzene, Ethan, 1981, pp. 4166CS–4167CS.

(List continued on next page.)

Primary Examiner—Nathan M. Nutter
Attorney, Agent, or Firm—Irell & Manella

[57] ABSTRACT

A method for sensitizing hypoxic tumor cells to radiation using derivatives of benzamide are disclosed. Some of the compounds useful in the method of the invention are novel.

13 Claims, 1 Drawing Sheet

OTHER PUBLICATIONS

Brown, *Radiation Research* 64:633–647 (1975).
Brown, *Radiation Research* 72:469–486 (1977).
Kennedy, *Anti-Cancer Drug Design* 2:181–194 (1987).
Brown, "Sensitizers in Radiotherapy," *Medical Radiology: Innovations in Radiation Oncology*, Berlin: Springer-Verlag, 1988.
Asquith et al., *Radiation Res.* (1974) 60:108–118.
Brown et al., *Radiation Res.* (1980) 82:171–190.
Calcutt et al., *Brit. J. Cancer* (1970) 24:380–388.
Hlavata et al., *Chem Abstract* (1980) 93:61755s.
Lunec et al., *Brit. J. Cancer* (1984) 49:19–25.
Miyakoshi et al., *Radiation Res.* (1985) 102:359–366.
Thraves et al., *Radiaiton Res.* (1985) 104:119–127.
Altman, (1983) Chemical Abstracts 99, No. 18898c.
Patil et al., (1976) Chemical Abstracts 85, No. 192613b.
Lichtenberger et al., (1963) Chemical Abstracts 58, No. 13900b.
Winstead et al., (1962) Chemical Abstracts 57, No. 11094i.
Coates et al., (1960) Chemical Abstracts 54, No. 13054e.

SUBSTITUTED BENZAMIDE RADIOSENSITIZERS

REFERENCE TO GOVERNMENT GRANT OR CONTRACT

The invention described herein was made in the course of work under grant or contract from the National Institutes of Health.

This application is a continuation of application Ser. No. 06/730,761, filed May 3, 1985, now abandoned.

TECHNICAL FIELD

The invention is in the field of radiotherapy. Specifically, it relates to sensitizing tumor cells to radiation using substituted benzamides.

BACKGROUND ART

Hypoxic tumor cell radiosensitizers are compounds that selectively increase the sensitivity of hypoxic cells in tumors to radiation. Various heterocyclic compounds, in particular, those with oxidized nitrogen moieties have been used for this purpose. Indeed, it has been postulated that the oxidized nitrogen functionality is responsible for this activity. Nitroimidazoles, particularly misonidazole (MIS) and metronidazole have been studied extensively, and MIS is commonly used as a standard in in vitro and in vivo tests for radiosensitizing activity. (See, e.g., Asquith, et al, *Radiation Res* (1974) 60:108-118; Hall, et al, *Brit J Cancer* (1978) 37:567-569; Brown, et al, *Radiation Res* (1980) 82:171-190; and U.S. Pat. No. 4,371,540. U.S. Ser. No. 439,435, filed Nov. 5, 1982 describes certain 1-substituted 3(5)-nitro-s-triazoles as hypoxic tumor cell radiosensitizers; U.S. Ser. Nos. 556,308 and 556,311, both filed Nov. 30, 1983 disclose similar radiosensitizing activity of quinoxaline-1,4-dioxide derivatives.

The present invention provides a new group of radiosensitizers that do not contain oxidized nitrogen—the substituted benzamides and their thio analogs. Some members of this group are known to be inhibitors of the enzyme poly(ADP-ribose)polymerase, which is believed to be essential in the repair of irradiated cells after radiation. Such "potential lethal damage repair". (PLDR) is, of course, effected after the radiation treatment, typically over the course of several hours. While the net effect of inhibiting PLDR may be to enhance cell killing, the mechanism for thus enhancing the effect of the radiation treatment is different from that of radiosensitization. Agents which inhibit PLDR must be present during the repair period, and their presence during the irradiation itself is not required. On the other hand, radiosensitizers must be present during the radiation treatment, and can be removed immediately thereafter, without change in their effect.

Accordingly, it was surprising that some benzamide compounds, known only to inhibit poly(ADP-ribose)-polymerase, exhibited a time dependence with respect to their effect on irradiated tumor cells which corresponds to that of the radiosensitizers.

DISCLOSURE OF THE INVENTION

The invention provides a valuable addition to the repertoire of compounds available as radiosensitizers for hypoxic tumor cells. Some of the compounds useful in this regard are known, others are novel. One aspect of the invention, therefore, is a method of radiosensitizing hypoxic tumor cells in a warm blooded animal comprising administering a compound of the formula:

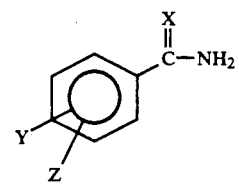

(1)

wherein
X is O or S;
Y is H, Me, OMe, OEt acetoxy or acetamido;
Z is OR or NHR in which R is H, straight chain alkyl (1-6C) optionally substituted with 1 or 2 substituents selected from the group consisting of halo, hydroxy, epoxy, alkoxy, amino, acyloxy and acylamido, and in which R can optionally be interrupted by a single ether (—O—) linkage; or O(CO)R or NH(CO)R in which R is as above defined.

Certain compounds of formula 1 wherein Z is in the 3-position, and wherein Z is OR or NHR in which R is substituted or interrupted with —O—, or O(CO)R or NH(CO)R in which R is substituted or interrupted with —O—, are novel. Therefore, in another aspect, the invention is directed to these compounds per se.

MODES OF CARRYING OUT THE INVENTION

Figure 2:
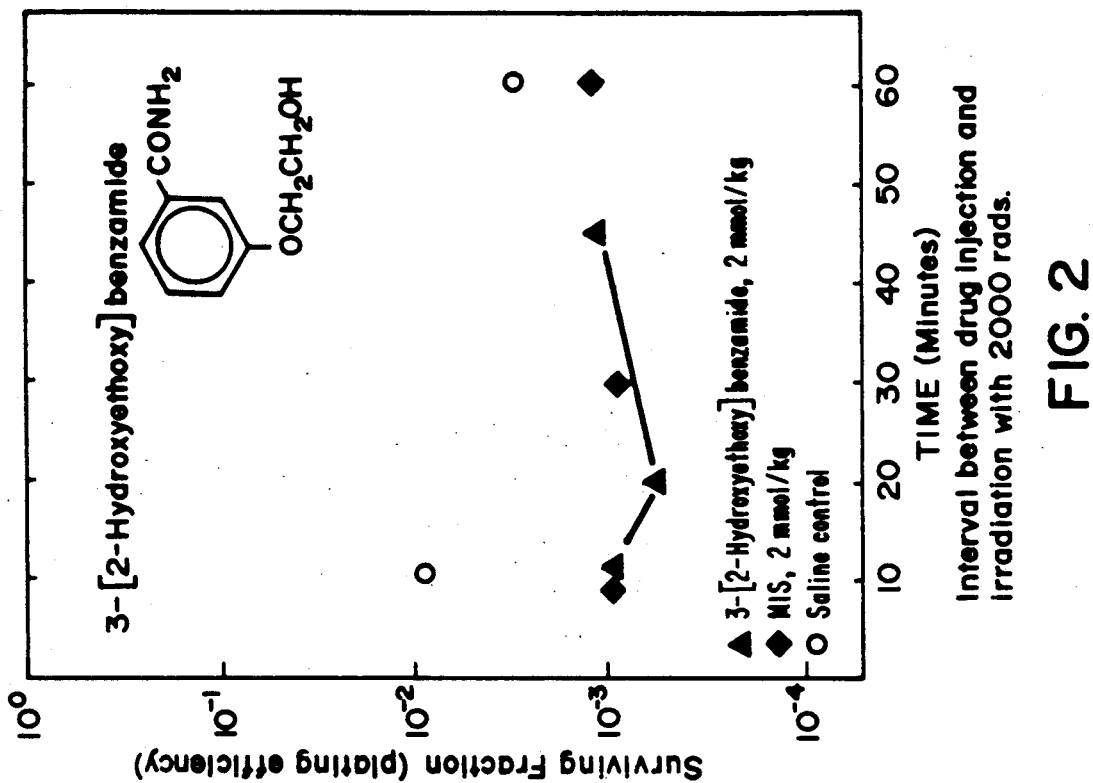
FIG. 2 shows similar results for 3-(2-hydroxyethoxy)-benzamide.

The compounds useful in radiosensitizing hypoxic tumor cells as described herein are derivatives of benzamide or the thio analogs thereof. The benzene ring of the benzamide or thiobenzamide may thus be substituted with one or two additional substituents. The substituent of formula Z is preferably in the 3 position; substituent Y preferentially in position 4. However, if substituent Z is in the 4 position, embodiments wherein Y is in position 3 are preferred. Especially preferred are those embodiments wherein X is O and those wherein Y is H—i.e., the compound of formula 1 is a monosubstituted benzamide or thiobenzamide.

The alkyl group represented by R may contain 1-6 carbon atoms, and may optionally be interrupted by a single ether linkage. Thus, the unsubstituted form of R can be, for example, methyl, ethyl, n-propyl, hexyl, 2-ethoxyethyl, 3(n-propoxy)propyl, 4-methyoxybutyl, and the like.

R may be substituted with one or two substituents. The halo substituents are fluoro, chloro, bromo, or iodo. The alkoxy substituents may contain 1 to 4 carbon atoms, and include, for example, methoxy, n-propoxy, and t-butoxy. The amino substituent may be $NH_2$, or NHR' where R' is an alkyl of 1-4 carbons. The acyloxy and acylamido groups are represented by R'COO and R'CONH, respectively, where R' contains 1-4 carbons.

A particularly preferred subset of compounds useful in the method of the invention are, in general, those wherein Y is H, Z is in the 3' position, and Z is either hydroxy or R contains 4 carbons or less.

Specific particularly preferred compounds include 2-hydroxybenzamide;
3-hydroxybenzamide;
4-hydroxybenzamide;
3-methoxybenzamide;
4-ethoxybenzamide;
3-(2-hydroxyethoxy)benzamide;
3-(4-acetamido-n-butanoxy)benzamide;
3-(3-amino-n-propanoxy)benzamide;
3-(2,3-epoxypropoxy)benzamide;
4-(2,3-epoxypropoxy)benzamide;
4-(3-methoxy-2-hydroxy-n-propoxy)benzamide;
3-(4-ethoxy-3-hydroxy-n-butoxy)benzamide;
3-(3,4-dihydroxy-n-butoxy)benzamide;
4-hydroxy-3-(3,4-dihydroxy-n-butoxy)benzamide;
3-ethoxy-4-(3,4-dihydroxy-n-butoxy)benzamide;
3-hydroxy-4-methoxybenzamide;
3-methyl-4-hydroxybenzamide;
4-ethyl-3-methoxybenzamide;
4-methyl-3-(2,3-dihydroxy-n-propoxy)benzamide;
3-methyl-4-(2,3-dihydroxy-n-propoxy)benzamide;
3-methoxy-4-(2,3-dihydroxy-n-propoxy)benzamide;
4-methoxy-3-(2,3-dihydroxy-n-propoxy)benzamide
4-methoxy-3-chloroacetamidobenzamide;
3-chloroacetamidobenzamide;
4-methyl-3-[(2-hydroxyethyloxy)acetamido]benzamide;
3-[(2-hydroxyethyloxy)acetamido]benzamide;
2,3-dimethyoxybenzamide;
3,4-dimethyoxybenzamide;
2,3-diethoxybenzamide;
3,4-diethoxybenzamide;
3,5-dimethoxybenzamide;
3,5-diacetamidobenzamide;
3,4-diacetamidobenzamide;
3-(2-acetoxyethoxy)benzamide;
4-hydroxy-3-(2-acetoxyethoxy)benzamide;
3-n-hexyloxybenzamide;

and the thioamide analogs of the foregoing list of compounds.

METHOD OF PREPARATION

Certain of the compounds of formula 1 are available as the benzoic acid analogs. These can be converted to the compounds of the invention by converting the carboxylic acid group to the corresponding amide.

Specifically, for example, 3-hydroxybenzoic acid can be converted to the corresponding 3-hydroxybenzamide by conventional reactions including treatment with SOCl$_2$, followed by reaction with ammonia.

The hydroxy substituent can be further modified by reaction with suitable alkylating agents. Thus, in general, the compounds of formula 1 may be prepared by the general reaction

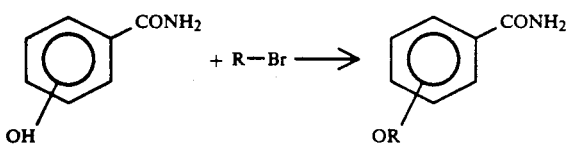

The reaction is carried out in the presence of base such as sodium or potassium carbonate in the presence of a suitable solvent, preferably an aprotic polar solvent such as dimethylformamide (DMF). The reaction can be carried out at approximately room to elevated temperature. Work-up and purification of products are carried out by conventional means.

To obtain the corresponding compounds of formula 1 wherein Z is NHR, the corresponding reaction using the amino benzamide starting material is used. Also, the presence of the Y substituent in the ring (where the desired component has Y other than H) does not interfere with the general preparation reaction.

It should be recalled that R may contain a substituent and it may then be desirable further to derivatize R. For example, where R contains a free hydroxyl group, the hydroxyl must be protected during the alkylation reaction by, for example, acetylation. The acetyl group may be retained in the compound of formula 1, or may be hydrolyzed to give the corresponding hydroxy compound.

Similarly, R may be obtained as an epoxide substituted alkyl, and the corresponding dihydroxy or alkoxy, hydroxy derivative prepared by hydrolysis.

The thioamide analogs of the invention are prepared by substituting for the benzamide derivative in the reactions set forth above the corresponding thiobenzamide derivatives. These can be obtained from the benzamide derivatives by standard means. In one preferred method the benzamide compound is treated with P$_2$S$_5$ in dioxane, substantially as described in Edwards, J. T., et al, *Canadian J Chem* (1977) 55:2331.

The compounds of formula 1, therefore, can be prepared from commercially available materials by methods known in the art. The conversions actually employed will, of course, depend on the nature of Y and R.

FORMULATION AND ADMINISTRATION

As demonstrated below, the substituted benzamides and thiobenzamides of the invention may be used to radiosensitize hypoxic tumor cells in warm-blooded animal hosts. While these radiosensitizers will typically be used in radiotherapy of human patients, they may be used to radiosensitize hypoxic tumor cells in other warm blooded animal species such as other primates, farm animals such as cattle, and sports animals and pets such as horses, dogs, and cats.

Hypoxia is believed to be associated with all types of solid malignant neoplasms. The benzamide or thiobenzamide may, therefore, be used to radiosensitize neoplastic epithelial cells, endothelial cells, connective tissue cells, bone cells, muscle cells, nerve cells, and brain cells. Examples of carcinomas and sarcomas that may be radiosensitized include carcinomas such as epithelial cell, acinic cell, alveolar cell, basal cell, basal squamous cell, cervical, renal, liver, Hurthle, Lucke, mucinous and Walker, and sarcomas such as Abernathy's, alveolar soft part, angiolithic, botyroid, encephaloid, endometria stroma, Ewing's fascicular, giant cell, lymphatic, Jensen's, juxtocortical osteogenic, Kaposi's, medullary, and synovial. Specific examples of tumors that have been radiosensitized with other radiosensitizers are reported in Adams, G. E., *Cancer: A Comprehensive Treatise* (F. Becker, Ed) Vol 6, pp 181–223, Plenum, N.Y., 1977.

The benzamides or thiobenzamides may be administered to patients orally or parenterally (intravenously, subcutaneously, intramuscularly, intraspinally, intraperitoneally, and the like). It is likely, however, that the preferred route for human administration will be intravenous. When administered parenterally they will normally be formulated in a unit dosage injectable form (solution, suspension, emulsion) with a pharmaceutically acceptable vehicle. Such vehicles are typically nontoxic and nontherapeutic. Examples of such vehicles are water, aqueous vehicles such as saline, Ringer's solution, dextrose solution, and Hanks' solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. When administered orally (or rectally) the compounds will usually be formulated into a unit dosage form such as a tablet, capsule, suppository or cachet. Such formulations typically include a solid, semisolid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, aginates, tragacanth, gelatin, syrup, methylcellulose, polyoxyethylene sorbitan monolaurate, methyl hydroxybenzoate, propyl hydroxybenzoate, talc, and magnesium stearate.

The amount of compound administered to the patient is sufficient to radiosensitize the malignant neoplasm to be treated but below that which may elicit toxic effects. This amount will depend upon the type of tumor, the species of the patient being treated, the indication dosage intended and the weight or body surface of the patient. The radiation may be administered to humans in a variety of different fractionation regimes, i.e., the total radiation dose is given in portions over a period of several days to several weeks. These are most likely to vary from daily (i.e., five times per week) doses for up to six weeks, to once weekly doses for four to eight weeks. An individual dose of the benzamide or thiobenzamide is given before each radiation treatment and is likely to be in the range of 0.01 to 20 mmol/kg and usually in the range of 0.1 to 2 mmol/kg.

Since tumor concentration of the administered compound is directly related to radiosensitivity, the compounds will ideally be administered at a time such that their peak concentration in the hypoxic cells occurs at a predictable time in relation to the time the tumor is exposed to radiation. This time will depend upon the manner in which the compound is administered, the particular dosage form employed, the type of tumor, and the speices of the patient. Intravenous administration will typically be done about ½ to about 1 hr prior to radiation exposure to provide maximum radiosensitization. Oral administration may require a somewhat longer lag because the benzamide or thiobenzamide must first pass through the gastrointestinal barrier.

EXAMPLES

The following examples further illustrate the benzamides and thiobenzamides of the invention and methods for synthesizing them and using them. These examples are not intended to limit the invention in any manner.

EXAMPLE 1

Preparation of 3-Hydroxybenzamide

Ten g (72.4 mmol) of 3-hydroxybenzoic acid and 10 ml $SOCl_2$ were mixed and allowed to stand for 1 hr, heated on a steam bath for 2 hr, and then cooled and diluted with 25 ml of benzene. The benzene was then evaporated in vacuo to dryness and the residue extracted with 2×50 ml benzene. The extracted residue was disolved in 25 ml tetrahydrofuran (THF) and this solution added dropwise over a period of 15 min to a stirred, cold (−10° C.) 50 ml solution of concentrated ammonia. The mixture was stirred with cooling for an hour and then at room temperature overnight.

The mixture was poured into an open dish and allowed to evaporate to a solid mass. The solid was triturated with 50 ml ice water, collected, and air dried to yield 6.4 g (64%) of the desired product 3-hydroxybenzamide, mp 160°–162° C. The identity of the product with the desired 3-hydroxybenzamide was further confirmed using thin layer chromatography (TLC).

EXAMPLE 2

Preparation of 3-(2-Acetoxyethoxy)benzamide 3.0 g (21.9 mmol) of the 3-hydroxybenzamide prepared in Example 1 and 5.7 g (41.2 mmol) of anhydrous potassium carbonate were added to a round bottom flask followed by 40 ml anhydrous DMF added by syringe. To this mixture was added 11.85 g (70.9 mmol, 7.8 cc) of 2-acetoyl ethyl bromide, also using a syringe to maintain anhydrous conditions. The suspension was stirred for 48 hr and the mixture filtered. The solid was washed with 6×5 ml DMF and the filtrate evaporated in vacuo to a solid. The resulting solid was recrystallized from 90% aqueous alcohol and the solid from the filtration was washed with cold 90% alcohol and ether. The desired product, 3-(2-acetoylethoxy)benzamide was obtained in 65% yield (3.2 g), mp 121°–122° C. Identity of the product was confirmed by TLC and by elemental analysis. Calculated for $C_{11}H_{13}NO_4$; C: 59.18; H: 5.87; N: 6.28; Found: C: 59.03; H: 5.83; N: 6.58.

EXAMPLE 3

Preparation of 3-(2-Hydroxyethoxy)benzamide 1.0 g (4.5 mmol) of the 3-(2-acetoxyethoxy)benzamide prepared in Example 1 was mixed with 2 g Amberlyst 15 and 50 ml methanol. The mixture was stirred for 40 hr and filtered. The filtrate was evaporated in vacuo to dryness and the residue disolved in 50 ml absolute ethanol and filtered to remove a small amount of insoluble material. The filtrate was evaporated in vacuo to obtain 750 mg of the white solid 3-(2-hydroxyethoxy)benzamide, representing 92% yield. The identity of the desired product was confirmed by TLC and elemental analysis: Calculated for $C_9H_{11}NO_3$; C: 59.65; H: 6.11; N: 7.73; Found: C: 59.56; H: 6.05; N: 7.70.

EXAMPLE 4

In Vivo Assay for Radiosensitization Activity

The compounds of the invention are tested in vivo for radiosensitization activity by the assay of Brown, J. M., *Radiation Res* (1975) 64:633–47, incorporated herein by reference. For this assay EMT6 tumors in female BALB/c mice weighing 20–25 g are used. These mice are bred under specific pathogen-free conditions and are 3–4 months old at the beginning of each experiment. The EMT6 tumor is grown intradermally in the flank from an inoculation of $2 \times 10^5$ tumor cells taken from the 2nd–8th in vitro passage of the tumor cells since removal from the previous in vivo tumor. Two tumors per mouse are implanted, and are used as subject tumors when they reach a volume of approximately 100 ml. At this point the tumors contain approximately 20% hypoxic cells.

Figure 1:
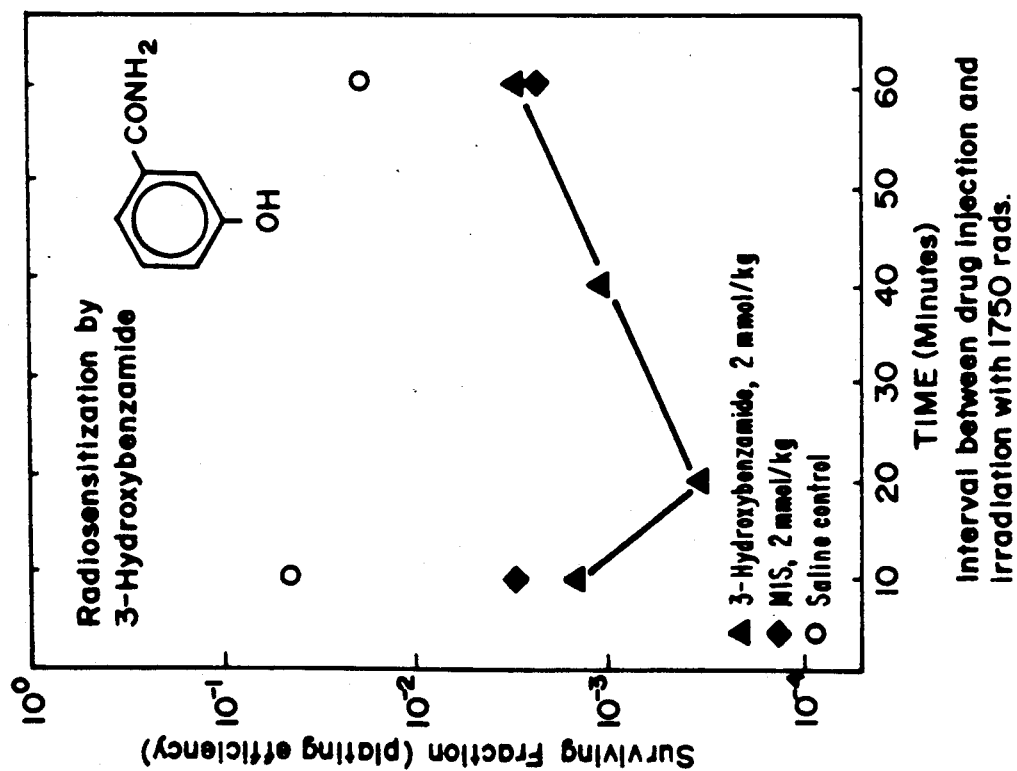
FIG. 1 shows the radiosensitizing effect of 3-hydroxybenzamide as compared to MIS.

Test compounds are compared against MIS in this assay. The test compound is tested at a fixed injected dose of either 5 mmole/kg or ⅔ of the $LD_{50}$ (whichever is lower), MIS is injected into controls at the same dose. Additional suitable controls of test compound-injected but non-irradiated and saline-injected and irradiated mice are also included. A fixed radiation dose of 2,000 rad is applied at variable intervals of 5 min to 2 hr between injection and irradiation. Typically, irradiation is applied at 5, 10, 15, 20, 30, 45, 60, 90, and 120 min following intraperitoneal administration of both drugs. By using these intervals, the results give an indication of both the optimum time to irradiate and of how the test compound sensitizes in relationship to MIS. The results of such time-course experiments using 3-hydroxybenzamide and 3-(2-hydroxyethoxy)benzamide are shown in FIGS. 1 and 2, respectively.

Irradiation of the EMT6 tumors is done by irradiating nonanesthetized tumor-bearing mice in a Plexiglas box. Irradiation conditions are 250 kVp X-rays, 15 mA, FSC 33 cm, added filtration of 0.35 mm Cu, half value layer 1.3 mm Cu, and a dose rate of 317 rad/min.

Radiosensitization activity is judged by survival rate of dissected and cultured tumor cells as follows: The tumor-bearing mice are killed immediately after irradiation, and tumors dissected from the skin, cut into several pieces, and made into a fine brei by high-speed chopping with a razor blade attached to a jigsaw. The brei is added to 30 ml of Hank's buffered salt solution (HBSS) containing 0.02% DNase, 0.05% promase, and 0.02% collagenase. The suspension is stirred for 30 min at 37° C., filtered, and centrifuged at 1,600 rmp for 10 min at 4° C. The cell pellet is resuspended in complete Waymouth's medium plus 12½% horse serum plus 2-12% fetal calf serum (FCS) and an aliquot mixed with trypan blue and counted with the use of a hemacytometer. Suitable dilutions of this serum plated into 60- or 100-mm polystyrene petri dishes (Lux Scientific Corp) in 5 or 15 ml of medium. After incubation for 13 days, the colonies are fixed and stained, and those containing 50 cells or more are counted. The dilution yielding an average count of 25-100 colonies in a 60 mm dish is used in calculation of results. The more highly diluted the sample to achieve this result, the less successful the killing and the less sensitizing the test compound.

The test compound is scored on the scale of 0 to 4 based on how it compares with MIS. The scoring system is:

0: No radiosensitization
1: Minimal radiosensitization (some radiosensitization relative to controls but lowest survival > 3 × lowest survival with MIS)
2: Moderate radiosensitization (not good as MIS, but lowest surviving fraction < 3 × lowest surviving fraction with MIS)
3: Good radiosensitization (equal to MIS)
4: Excellent radiosensitization (superior to MIS)

EXAMPLE 5

Cytotoxicity Tests

Cytotoxicity tests were also carried out on each of the compounds. The test procedure was as follows: Log-phase Chinese hamster ovary HA-1 cells were trypsinized (0.5% trypsin in Hank's buffered salt solution (HBSS)) and plated in 60 mm Permanox petri dishes in concentrations necessary to yield approximately 30 colonies after experimental treatment. The cells were allowed to attach overnight. Then the medium was removed from each dish and replaced with 2 ml of medium containing varying concentrations of the test compound. The petri dishes were then placed in nylon chamber fitted with gassing ports and, to achieve hypx=oxia, were gassed at room temperature with humidified $N_2$ containing 5% $CO_2$ for 1 hr at a rate of 1 l/min. The cells are then exposed to 10 mM of the test compound for 1 hr at 22° C. The % cell survival is read after such treatment.

EXAMPLE 6

Determination of $LD_{50}$ $LD_{50}$ is determined in BALB/c female mice (weighing 20-25 g) following intraperitoneal (ip) injection, unless the compound tested has low lipophilicty and is very soluble, wherein intravenous (iv) administration is used. Whichever is used, the radiosensitization and pharmacokinetic assays are performed using the same route of administration. $LD_{50}$ values at 1, 2, 5, and 60 days are determined by administering graded doses of the drug dissolved in physiological saline immediately prior to injection.

EXAMPLE 7

Results

The results of the assay of Examples 4 and 5 are as follows:

| Compound | Cytotoxicity % Cell Survival | Radio-sensitization |
|---|---|---|
| 3-hydroxybenzamide | 90, 77 | 3 |
| 3-(2-hydroxyethoxy)benzamide | 89 | 3 |

In the sensitivity assay of Example 4, each of 3-hydroxybenzamide, 3-(2-hydroxyethoxy)benzamide, and 3-(2-acetoylethoxy)benzamide gave a sensitizer enhancement ratio of 1.6 at a 1-2 mM concentration, which is comparable to that for MIS.

Modifications of the above described modes for carrying out the invention that are apparent to those of skill in the chemical, pharmaceutical, medical, and related arts are intended to be within the scope of the following claims.

We claim:

1. A method to destroy hypoxic tumor cells in a warm-blooded animal, which method comprises
(a) administering to said warm-blooded animal a compound of the formula:

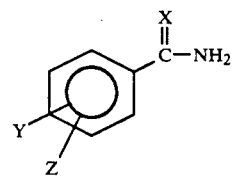

wherein
X is O or S;
Y is H, Me, OMe, OEt, acetoxy or acetamido; and
Z is OR, NHR, O(CO)R or NH(CO)R in which R is H, straight chain alkyl (1-6C) optionally substituted with 1 or 2 substituents selected from the group consisting of halo, hydroxy, epoxy, alkoxy (1-4C), amino, acyloxy (1-4C) and acylamido (1-4C), and in which R can optionally be interrupted by a single ether linkage; in an amount effective to radiosensitize said hypoxic tumor cells, (b) followed by, after a time period to provide maximum radiosensitization, irradiating said tumor cells with a dose of radiation effective to destroy said cells.

2. The method of claim 1 wherein X is O.

3. The method of claim 1 wherein Y is H.

4. The method of claim 1 wherein the compound of formula (1) has Z in the 3-position relative to the amide or thioamide.

5. The method of claim 1 wherein the compound of formula (1) is 3-hydroxybenzamide, 3-(2-hydroxyethoxy)benzamide or 3-(2-acetoxyethoxy)benzamide.

6. The method of claim 1 wherein the compound of formula (1) is 3- or 4-(2,3-epoxy-n-propoxy)benzamide.

7. The method of claim 1 wherein the compound of formula (1) is 3- or 4-(2-hydroxy-3-methoxy-n-propoxy)benzamide.

8. The method of claim 1 wherein the compound of formula (1) is 3-methoxythiobenzamide or 3-hydroxythiobenzamide.

9. The method of claim 1 wherein the compound of formula (1) is 3-(chloroacetamido)benzamide.

10. The method of claim 1 wherein the compound of formula (1) is 3-[(2-hydroxyethoxy)acetamido]benzamide.

11. The method of claim 1 wherein the compound of formula (1) is selected from the group consisting of
3-hydroxy-4-methoxybenzamide,
3-(2,3-dihydroxy-n-propoxy)-4-methoxybenzamide,
3-(2,3-dihydroxy-n-propoxy)-4-methylbenzamide,
4-(2,3-dihydroxy-n-propoxy)-4-methoxybenzamide.

12. The method of claim 1 wherein the effective amount of the compound of formula 1 is in the range of 0.01–20 mmol/kg.

13. The method of claim 1 wherein the time effective to provide maximum radiosensitization is one-half hour to one hour.

* * * * *